(12) United States Patent
Kollar et al.

(10) Patent No.: US 11,730,480 B2
(45) Date of Patent: Aug. 22, 2023

(54) METHOD AND APPARATUS FOR ACCESSING MATTER DISPOSED WITHIN AN INTERNAL BODY VESSEL

(71) Applicant: Covidien LP, Mansfield, MA (US)

(72) Inventors: Charles Kollar, West Hartford, CT (US); Haley Strassner, Hamden, CT (US)

(73) Assignee: Covidien LP, Mansfield, MA (US)

( * ) Notice: Subject to any disclaimer, the term of this patent is extended or adjusted under 35 U.S.C. 154(b) by 738 days.

(21) Appl. No.: 16/540,165

(22) Filed: Aug. 14, 2019

(65) Prior Publication Data

US 2020/0085441 A1 Mar. 19, 2020

Related U.S. Application Data

(60) Provisional application No. 62/731,138, filed on Sep. 14, 2018.

(51) Int. Cl.
| | | |
|---|---|---|
| *A61B 17/115* | (2006.01) | |
| *A61B 17/11* | (2006.01) | |
| *A61B 90/00* | (2016.01) | |
| *A61B 17/00* | (2006.01) | |

(52) U.S. Cl.
CPC ....... *A61B 17/1155* (2013.01); *A61B 17/1114* (2013.01); *A61B 90/08* (2016.02); *A61B 2017/00477* (2013.01); *A61B 2090/08021* (2016.02)

(58) Field of Classification Search
CPC . A61B 17/1155; A61B 17/1114; A61B 90/08; A61B 2017/00477; A61B 2090/08021
See application file for complete search history.

(56) References Cited

U.S. PATENT DOCUMENTS

| | | | |
|---|---|---|---|
| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |

(Continued)

FOREIGN PATENT DOCUMENTS

| | | |
|---|---|---|
| DE | 25796 C | 1/1884 |
| DE | 3542667 A1 | 6/1986 |

(Continued)

OTHER PUBLICATIONS

European Search Report EP 12191639.9 dated Feb. 20, 2013.

(Continued)

*Primary Examiner* — Brooke Labranche
(74) *Attorney, Agent, or Firm* — Carter, DeLuca & Farrell LLP

(57) ABSTRACT

A wound protector is provided for use with a surgical stapling instrument. One end of the wound protector is attached to the surgical stapling instrument, with the other end free and able to move to encompass the distal portion of the surgical stapling instrument after use. In this way, any contaminants on the distal portion of the circular stapling instrument are prevented from contacting healthy tissue as the surgical stapling instrument is removed from a patient's body.

5 Claims, 7 Drawing Sheets

(56) References Cited

U.S. PATENT DOCUMENTS

| | | |
|---|---|---|
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |

(56) References Cited

U.S. PATENT DOCUMENTS

| | | | |
|---|---|---|---|
| 8,388,630 B2 | 3/2013 | Teague et al. | |
| 8,409,112 B2 | 4/2013 | Wynne et al. | |
| 8,409,216 B2 | 4/2013 | Parihar et al. | |
| 8,409,217 B2 | 4/2013 | Parihar et al. | |
| 8,414,596 B2 | 4/2013 | Parihar et al. | |
| 8,419,749 B2 | 4/2013 | Shelton, IV et al. | |
| 8,425,533 B2 | 4/2013 | Parihar et al. | |
| 8,430,826 B2 | 4/2013 | Uznanski et al. | |
| 8,435,237 B2 | 5/2013 | Bahney | |
| 8,444,655 B2 | 5/2013 | Parihar et al. | |
| 8,579,914 B2 | 11/2013 | Menn et al. | |
| 8,585,712 B2 | 11/2013 | O'Prey et al. | |
| 8,591,521 B2 | 11/2013 | Cherry et al. | |
| 8,652,147 B2 | 2/2014 | Hart | |
| 8,696,683 B2 | 4/2014 | LeVert | |
| 8,721,658 B2 | 5/2014 | Kahle et al. | |
| 8,734,464 B2 | 5/2014 | Grover et al. | |
| 8,777,961 B2 | 7/2014 | Cabrera et al. | |
| 8,795,291 B2 | 8/2014 | Davis et al. | |
| 8,821,377 B2 | 9/2014 | Collins | |
| 8,827,968 B2 | 9/2014 | Taylor et al. | |
| 8,870,894 B2 | 10/2014 | Taylor et al. | |
| 8,906,035 B2 | 12/2014 | Zwolinski et al. | |
| 8,906,036 B2 | 12/2014 | Farascioni | |
| 8,956,370 B2 | 2/2015 | Taylor et al. | |
| 8,968,329 B2 | 3/2015 | Cabrera | |
| 9,662,115 B2 * | 5/2017 | Prior | A61B 17/3423 |
| 2002/0068943 A1 | 6/2002 | Chu et al. | |
| 2002/0082516 A1 | 6/2002 | Stefanchik | |
| 2003/0073970 A1 | 4/2003 | Suga | |
| 2003/0100909 A1 | 5/2003 | Suzuki | |
| 2003/0100919 A1 | 5/2003 | Hopkins et al. | |
| 2003/0199915 A1 | 10/2003 | Shimm | |
| 2003/0216773 A1 | 11/2003 | Shimm | |
| 2004/0097960 A1 | 5/2004 | Terachi et al. | |
| 2004/0138587 A1 | 7/2004 | Lyons | |
| 2005/0085808 A1 | 4/2005 | Nakao | |
| 2005/0165411 A1 | 7/2005 | Orban | |
| 2005/0256425 A1 | 11/2005 | Prusiner | |
| 2005/0267492 A1 | 12/2005 | Poncet et al. | |
| 2006/0030750 A1 | 2/2006 | Amer | |
| 2006/0052799 A1 | 3/2006 | Middleman et al. | |
| 2006/0058776 A1 | 3/2006 | Bilsbury | |
| 2006/0169287 A1 | 8/2006 | Harrison et al. | |
| 2006/0200169 A1 | 9/2006 | Sniffin | |
| 2006/0200170 A1 | 9/2006 | Aranyi | |
| 2006/0229639 A1 | 10/2006 | Whitfield | |
| 2006/0229640 A1 | 10/2006 | Whitfield | |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2007/0186935 A1 | 8/2007 | Wang et al. | |
| 2008/0188766 A1 | 8/2008 | Gertner | |
| 2008/0221587 A1 | 9/2008 | Schwartz | |
| 2008/0221588 A1 | 9/2008 | Hollis et al. | |
| 2008/0234696 A1 | 9/2008 | Taylor et al. | |
| 2008/0255597 A1 | 10/2008 | Pravong et al. | |
| 2008/0300621 A1 | 12/2008 | Hopkins et al. | |
| 2008/0312496 A1 | 12/2008 | Zwolinski | |
| 2009/0043315 A1 | 2/2009 | Moon | |
| 2009/0082779 A1 | 3/2009 | Nakao | |
| 2009/0182292 A1 | 7/2009 | Egle et al. | |
| 2009/0192510 A1 | 7/2009 | Bahney | |
| 2009/0240238 A1 | 9/2009 | Grodrian et al. | |
| 2010/0000471 A1 | 1/2010 | Hibbard | |
| 2010/0152746 A1 | 6/2010 | Ceniccola et al. | |
| 2011/0087235 A1 | 4/2011 | Taylor et al. | |
| 2011/0184311 A1 | 7/2011 | Parihar et al. | |
| 2011/0184434 A1 | 7/2011 | Parihar et al. | |
| 2011/0184435 A1 | 7/2011 | Parihar et al. | |
| 2011/0184436 A1 | 7/2011 | Shelton, IV et al. | |
| 2011/0190779 A1 | 8/2011 | Gell et al. | |
| 2011/0190781 A1 | 8/2011 | Collier et al. | |
| 2011/0190782 A1 | 8/2011 | Fleming et al. | |
| 2011/0264091 A1 | 10/2011 | Koppleman et al. | |
| 2011/0299799 A1 | 12/2011 | Towe | |
| 2012/0046667 A1 | 2/2012 | Cherry et al. | |
| 2012/0083795 A1 | 4/2012 | Fleming et al. | |
| 2012/0083796 A1 | 4/2012 | Grover et al. | |
| 2012/0203241 A1 | 8/2012 | Williamson, IV | |
| 2013/0023895 A1 | 1/2013 | Saleh | |
| 2013/0103042 A1 | 4/2013 | Davis | |
| 2013/0116592 A1 | 5/2013 | Whitfield | |
| 2013/0184536 A1 | 7/2013 | Shibley et al. | |
| 2013/0190773 A1 | 7/2013 | Carlson | |
| 2013/0218170 A1 | 8/2013 | Uznanski et al. | |
| 2013/0245636 A1 | 9/2013 | Jansen | |
| 2013/0274758 A1 | 10/2013 | Young et al. | |
| 2013/0325025 A1 | 12/2013 | Hathaway et al. | |
| 2014/0046337 A1 | 2/2014 | O'Prey et al. | |
| 2014/0058403 A1 | 2/2014 | Menn et al. | |
| 2014/0180303 A1 | 6/2014 | Duncan et al. | |
| 2014/0222016 A1 | 8/2014 | Grover et al. | |
| 2014/0236110 A1 | 8/2014 | Taylor et al. | |
| 2014/0243865 A1 | 8/2014 | Swayze et al. | |
| 2014/0249541 A1 | 9/2014 | Kahle et al. | |
| 2014/0276913 A1 | 9/2014 | Tah et al. | |
| 2014/0303640 A1 | 10/2014 | Davis et al. | |
| 2014/0309656 A1 | 10/2014 | Gal et al. | |
| 2014/0330285 A1 | 11/2014 | Rosenblatt et al. | |
| 2014/0350567 A1 | 11/2014 | Schmitz et al. | |
| 2014/0371759 A1 | 12/2014 | Hartoumbekis | |
| 2014/0371760 A1 | 12/2014 | Menn | |
| 2015/0018837 A1 | 1/2015 | Sartor et al. | |
| 2015/0045808 A1 | 2/2015 | Farascioni | |
| 2017/0049427 A1 | 2/2017 | Do et al. | |
| 2017/0215904 A1 | 8/2017 | Wassef et al. | |
| 2017/0224321 A1 | 8/2017 | Kessler et al. | |
| 2017/0325798 A1 | 11/2017 | Prior | |
| 2018/0242975 A1 * | 8/2018 | Penna | A61B 46/10 |

FOREIGN PATENT DOCUMENTS

| | | |
|---|---|---|
| DE | 8435489 U1 | 8/1986 |
| DE | 4204210 A1 | 8/1992 |
| DE | 19624826 A1 | 1/1998 |
| DE | 10327106 A1 | 12/2004 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| EP | 2583629 A2 | 4/2013 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2013075103 A1 | 5/2013 |
| WO | 2014134285 A1 | 9/2014 |
| WO | 2015134888 A1 | 9/2015 |
| WO | 2017189442 A1 | 11/2017 |

OTHER PUBLICATIONS

European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.

(56) References Cited

OTHER PUBLICATIONS http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.
Extended European Search Report issued in corresponding Appl. No. EP 19170619.1 dated Sep. 19, 2019 (8 pages).

\* cited by examiner

METHOD AND APPARATUS FOR ACCESSING MATTER DISPOSED WITHIN AN INTERNAL BODY VESSEL

CROSS-REFERENCE TO RELATED APPLICATIONS

This application claims the benefit of and priority to U.S. Provisional Patent Application Ser. No. 62/731,138 filed Sep. 14, 2018, the entire disclosure of which is incorporated by reference herein.

TECHNICAL FIELD

The present disclosure generally relates to a surgical procedure and associated apparatus for accessing internal body vessels. More specifically, the present disclosure relates to an apparatus for both wound protection and specimen retrieval that minimizes the risk of contamination/infection to a patient.

BACKGROUND

Diseased gastrointestinal tissue sometimes must be removed, such as in cases of diverticulitis, cancer, and ischemic bowel. The procedure may be completed laparoscopically using surgical stapling instruments to transect out the unhealthy tissue and seal the tissue shut to prevent leakage of luminal content into the abdominal cavity and to provide hemostasis. Before the diseased tissue can be removed from the body, blood vessels and connective tissue to the diseased tissue are cut and sealed. Once the diseased tissue is separated from the blood vessels, connective tissue, and healthy tissue, it is removed from the body through the abdomen wall.

In order to restore the gastrointestinal (GI) tract, the oral and aboral ends of where the diseased tissue was removed must be anastomosed either using a suturing technique or an end-to-end anastomosis (EEA) stapler. The EEA stapler is used to staple together two tubular tissue structures using a circular pattern. When a circular stapler is used in a thoracic procedure, the surgeon first introduces the instrument through an incision into the thoracic cavity. The surgeon then creates an enterostomy to introduce the circular stapler into the gastrointestinal tract.

Once the circular stapler enters the GI tract, the stapler, as well as the specimen being resected, become unsterile. When the instrument and the specimen exit the patient through the thoracic cavity and incision, this can increase the likelihood of infection.

Improved wound protectors and specimen bags for use in minimally invasive surgical procedures remain desirable.

SUMMARY

The present disclosure is directed to a surgical stapling instrument suitable for accessing the interior of an intestine, the surgical stapling instrument possessing a wound protector thereon, which may be used to both remove tissue from within the intestine and provide a sterile cover of the end of the surgical stapling instrument within the intestine, thereby protecting sterile areas from both the contaminated specimen and contaminated portions of the surgical stapling instrument upon removal of the surgical stapling instrument from the patient's body.

In embodiments, a surgical stapling instrument includes a handle; an end effector including a stapling apparatus; and an adapter connecting the handle and the end effector. The surgical stapling instrument also includes a wound protector having a tubular body possessing a proximal portion and a distal portion, the tubular body defining a longitudinal bore that extends between the proximal portion and the distal portion of the tubular body, the adapter passing through the longitudinal bore of the tubular body; and a fixation ring attaching the distal portion of the tubular body to the adapter.

In embodiments, the proximal portion of the tubular body defines an opening, and the surgical stapling instrument further includes a pull string at the proximal portion of the tubular body about the opening.

Methods for using the surgical stapling instruments of the present disclosure are also provided. In embodiments, such methods include creating an opening extending through an abdominal wall of an abdominal cavity; accessing a first segment of an intestine within the abdominal cavity; advancing a stapling instrument through a first intestinal end segment of the first segment of the intestine and through a second intestinal end segment of a second segment of the intestine; and firing the stapling instrument to deliver fasteners through the first intestinal end segment of the intestine and the second intestinal end segment of the intestine to join the first and second intestinal end segments. The method further includes grasping a wound protector encompassing a portion of the stapling instrument; pulling the wound protector distally so that the wound protector everts over and covers a distal portion of the stapling instrument; closing the wound protector so that the distal portion of the stapling instrument is contained within the wound protector; and removing the stapling instrument from the intestine and the abdominal cavity.

In some embodiments, the method further includes approximating an anvil head of the stapling instrument relative to a staple cartridge of the stapling instrument to clamp the first and second intestinal end segments between the anvil head and the staple cartridge.

In embodiments, pulling the wound protector distally covers the anvil head and the staple cartridge of the stapling instrument.

In other embodiments, firing the stapling instrument includes delivering an annular array of staples from the staple cartridge to the anvil head to at least partially deform the annular array of staples.

In some embodiments, pulling the wound protector distally so that the wound protector everts over and covers the stapling instrument also includes covering a tissue specimen.

In other embodiments, closing the wound protector contains the tissue specimen within the wound protector.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
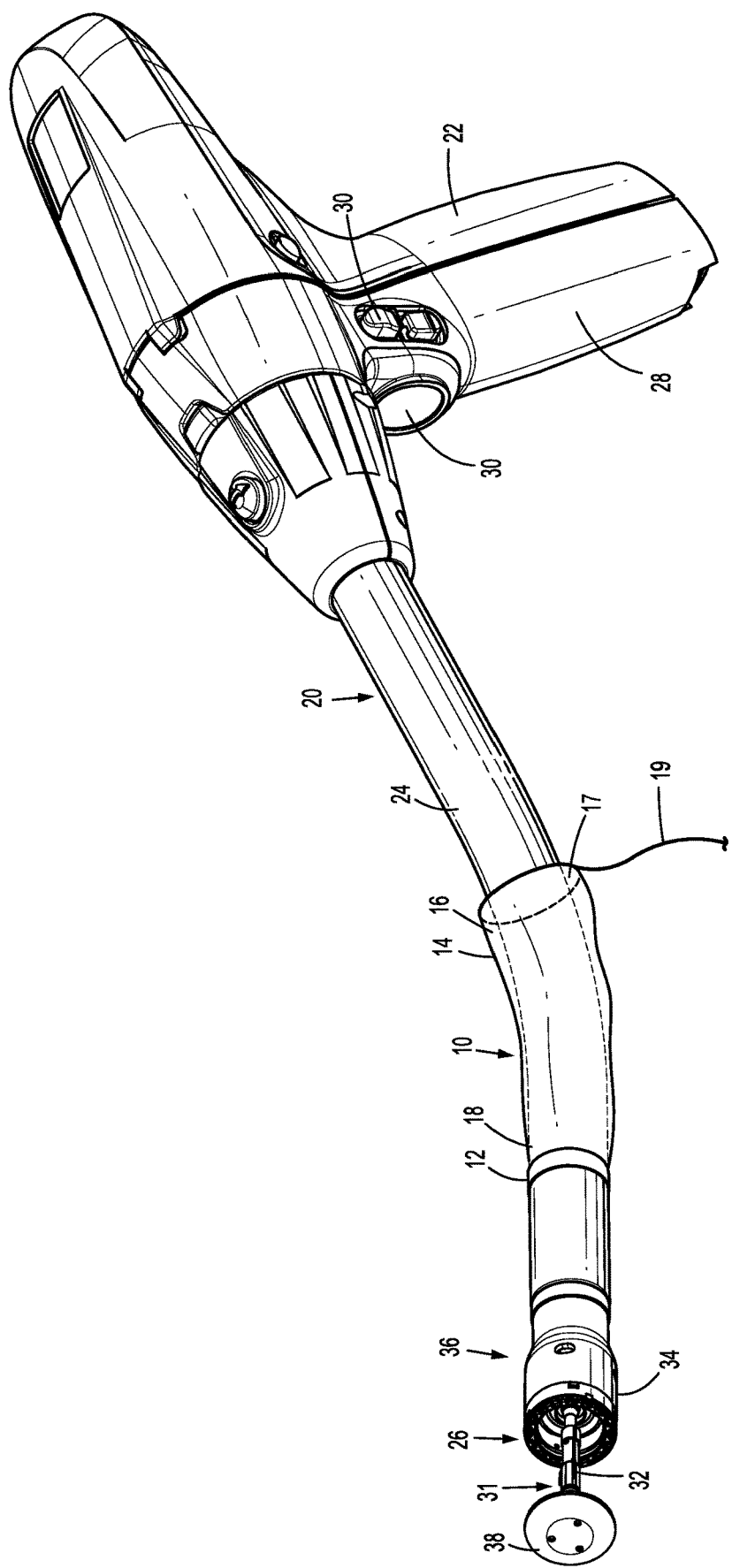
FIG. 1 is a perspective view of an exemplary embodiment of a surgical circular stapling instrument including a wound protector of the present disclosure.

The present disclosure provides specimen retrieval devices for use in minimally invasive surgical procedures. As used herein with reference to the present disclosure, minimally invasive surgical procedures encompass enterostomies, cholecystectomies, appendectomies, nephrectomies, colectomies, splenectomies, and the like. While the following discussion focuses on methodologies and associated apparatus(es) in performing an anastomosis, particularly in securing the end margins of two sections of the gastrointestinal (GI) tract to be joined after removal of a diseased section that was previously between the two sections of the GI tract, the apparatus of the present disclosure may be used in any other minimally invasive procedure to minimize contamination and/or the risk of infections that may occur as a specimen or any portion of an apparatus used in such a procedure has become contaminated.

The presently disclosed specimen retrieval devices will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel. In the following description, well-known functions or constructions are not described in detail to avoid obscuring the present disclosure in unnecessary detail.

Generally, the wound protector of the present disclosure may be used in conjunction with a medical device, in embodiments a surgical stapling instrument such as a circular stapling instrument. These circular stapling instruments include a handle, an elongated shaft with an end effector including a stapling apparatus having a cartridge assembly and an anvil assembly. In use, the opposed tissue end margins of the organ sections are clamped between the anvil assembly and the cartridge assembly. The instrument is fired which drives an annular array of staples from the cartridge assembly through the tissue end margins of the organ sections for deformation against the anvil. An annular knife within the staple holding component is advanced to core or remove organ tissue interior of the staples to clear the internal tubular passage. Thereafter, the anvil head may be tilted relative to the anvil center rod and the anvil assembly is withdrawn relative to the attached organ sections. An example of an instrument for performing circular anastomosis of tissue is disclosed in commonly assigned U.S. Pat. No. 9,750,503, the entire contents of which is incorporated by reference herein.

Figure 2:
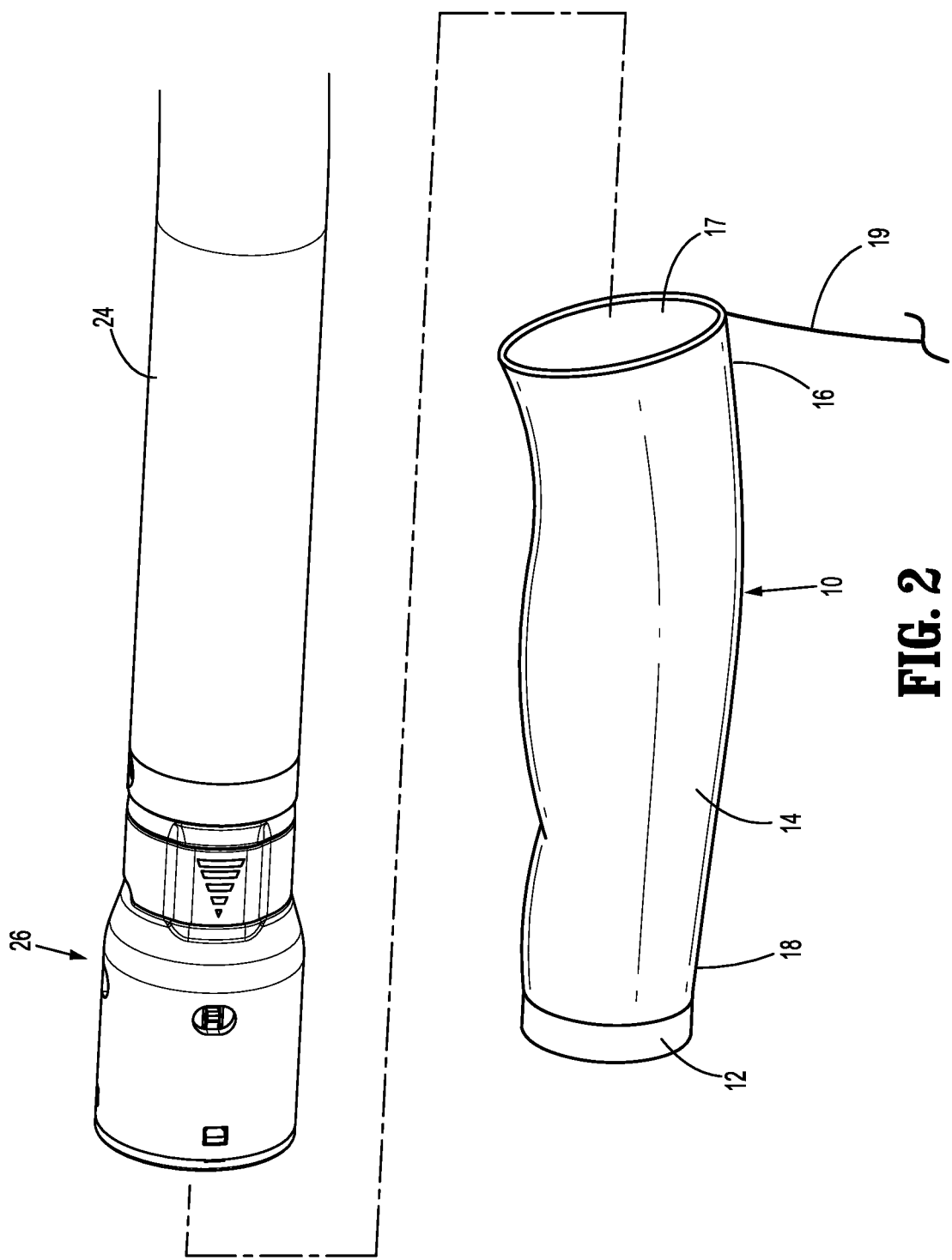
FIG. 2 is an exploded view showing a distal portion of the surgical circular stapling instrument and the wound protector of FIG. 1.

Referring now to FIGS. 1-7, and initially with reference to FIGS. 1-2, a wound protector 10 in accordance with an exemplary embodiment of the present disclosure is affixed to a circular stapling instrument 20. The circular stapling instrument 20 includes a handle assembly 22, an adapter 24 extending from the handle 22, and an end effector 26 coupled to the adapter 24. In embodiments, the handle 22 may be electrically powered including a motor and associated gears and linkages to control operation of the stapling instrument 20. The grip 28 may support a battery pack (not shown) which powers the handle 22. In other embodiments, the circular stapling instrument 20 may be powered via an external power source. The handle 22 incorporates a grip 28 and a plurality of actuation buttons 30 which may be activated to control various functions of the stapling instrument 20 including, e.g., approximation of the end effector 26 and firing of staples. In embodiments, the adapter 24 is releasably coupled to the handle 22 and includes a plurality of drive mechanisms (not shown) that translate power from the handle 22 to the end effector 26 in response to actuation of the actuation buttons 30 to effect operation, e.g., approximation and firing, of the end effector 26. Alternately, the adapter 24 may be non-removably secured to the handle 22. The adapter 24 also includes an anvil retainer 32 that extends from a distal portion of the adapter 24 and is movable between retracted and advanced positions. The anvil retainer 32 is couplable to the end effector 26. Commonly assigned U.S. Pat. Nos. 9,247,940; 9,055,943; and 8,806,973, and U.S. Publication No. 2015/0014392 disclose exemplary embodiments of powered handles and adapters suitable for use with the stapling instrument 20, and which are incorporated in their respective entireties by reference herein.

It is also envisioned that the handle 22 may be manually powered. Examples of manually powered handle assemblies are described in commonly assigned U.S. Pat. Nos. 8,789,737; 8,424,535; and 8,360,295, which are incorporated in their respective entireties by reference herein.

The end effector 26 includes a stapling apparatus including a cartridge assembly 34 and an anvil assembly 31 couplable relative to the cartridge assembly 34. In general, the cartridge assembly 34 incorporates a cartridge housing 36, one or more annular rows of staples (not shown) within the cartridge housing 36, staple pushers (not shown) for advancing the staples through the tissue end margins of the tubular organ sections and an annular knife (not shown in FIG. 1) internal of the staples to sever and remove excess organ tissue within the tubular organ sections upon advancement of the annular knife during, or subsequent to, deployment of the staples.

Figure 5:
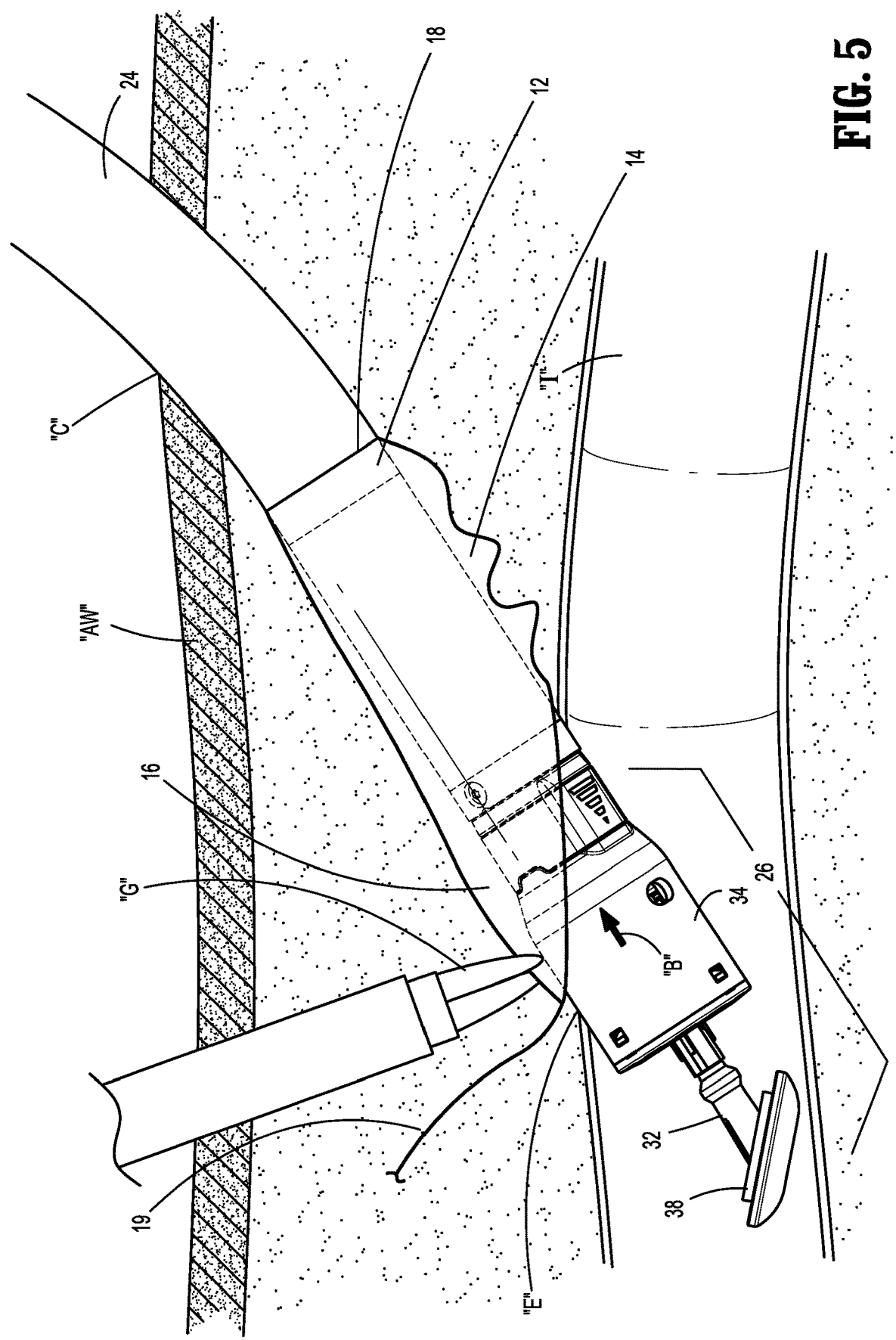
FIG. 5 is a side view of the distal portion of the circular stapling instrument including the wound protector shown in FIG. 1 during a surgical procedure as the wound protector is being deployed.

Referring now to FIGS. 1 and 5, the anvil assembly 31 of the end effector 26 will be discussed. The anvil assembly 31 shares some common features with the anvil assembly disclosed in commonly assigned U.S. Pat. No. 8,540,132, the entire disclosure of which is incorporated by reference herein. The anvil assembly 31 includes an anvil center rod 32 and an anvil head 38 pivotally mounted to the anvil center rod 32. The anvil head 38 is adapted to pivot relative to the anvil center rod 32 between a first operative condition in opposition to the cartridge assembly 34 (as depicted in FIG. 1) and a second pivoted or tilted condition, and may be normally biased to the second titled condition via a spring-biased plunger mechanism (not shown).

As depicted in FIGS. 1 and 2, the wound protector 10 includes a tubular body 14 having a having a proximal portion 16 and a distal portion 18, and defines a longitudinal bore 17 that extends between the proximal portion 16 and the distal portion 18. As shown in FIG. 1, the adapter 24 of the circular stapling instrument 20 passes through the longitudinal bore 17 of the tubular body 14. The distal portion 18 of the tubular body 14 is attached to the adapter 24 of the circular stapling instrument 20 by a fixation ring 12. The tubular body 14 also has a pull string 19 at the proximal portion 16 of the tubular body 14 for closing an opening defined at the proximal portion of the tubular body 14. In embodiments, the pull string 19 may be received in a cuff (not shown) formed at the proximal portion 16 of the tubular body 14.

The tubular body 14 of the wound protector 10 may be made from any suitable biocompatible material (e.g., nylon, urethane, ripstop nylon or latex) capable of forming a flexible collapsible member, or membrane. In embodiments, the material from which the specimen bag is made is resilient, antistatic, pyrogen-free, non-toxic, and sterilizable. Materials used to form the tubular body 14 may be opaque or clear.

Figure 3:
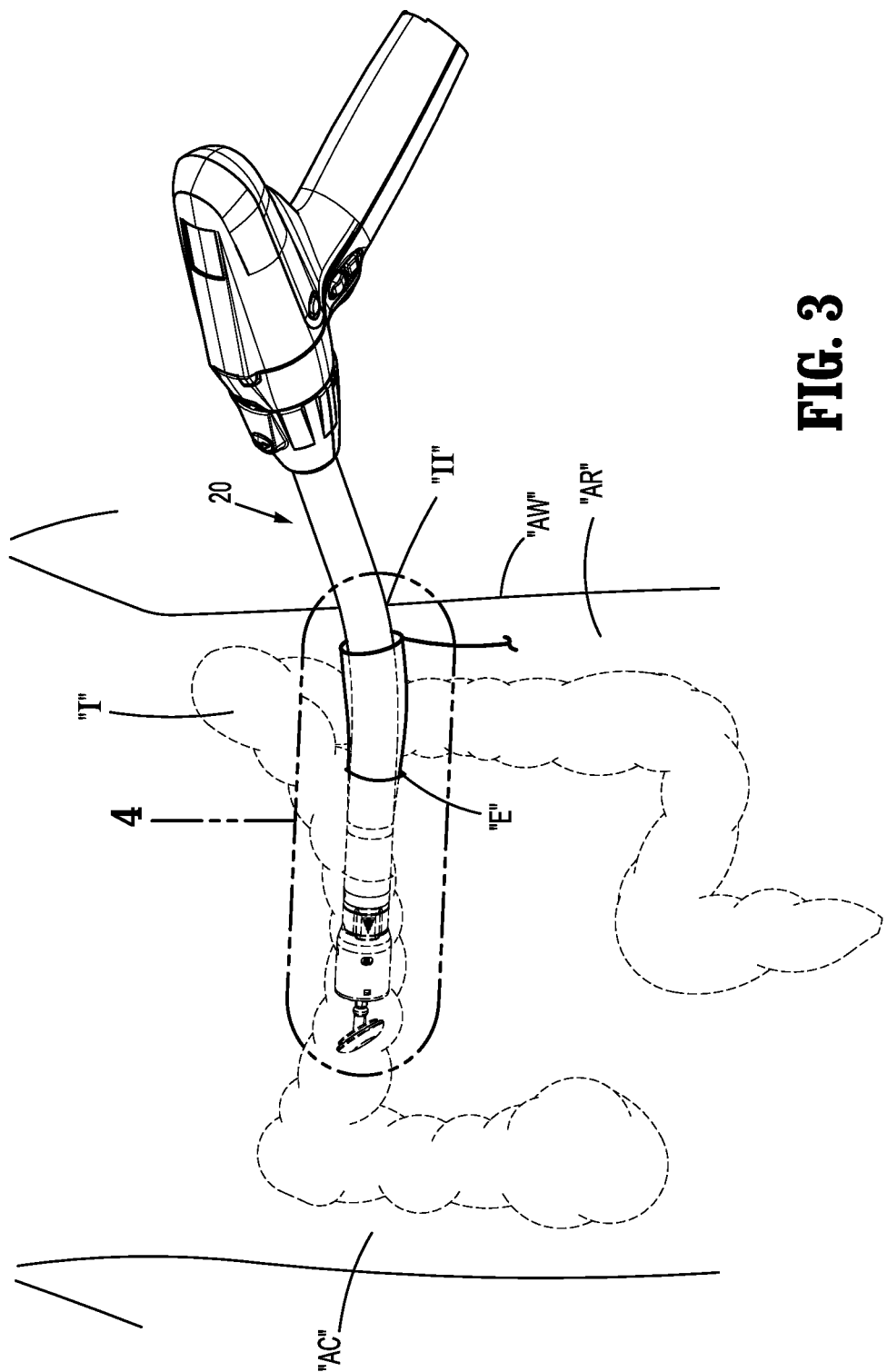
FIG. 3 is a side view showing the introduction of the surgical circular stapling instrument of FIG. 1 into a patient's body and intestine.
Figure 4:
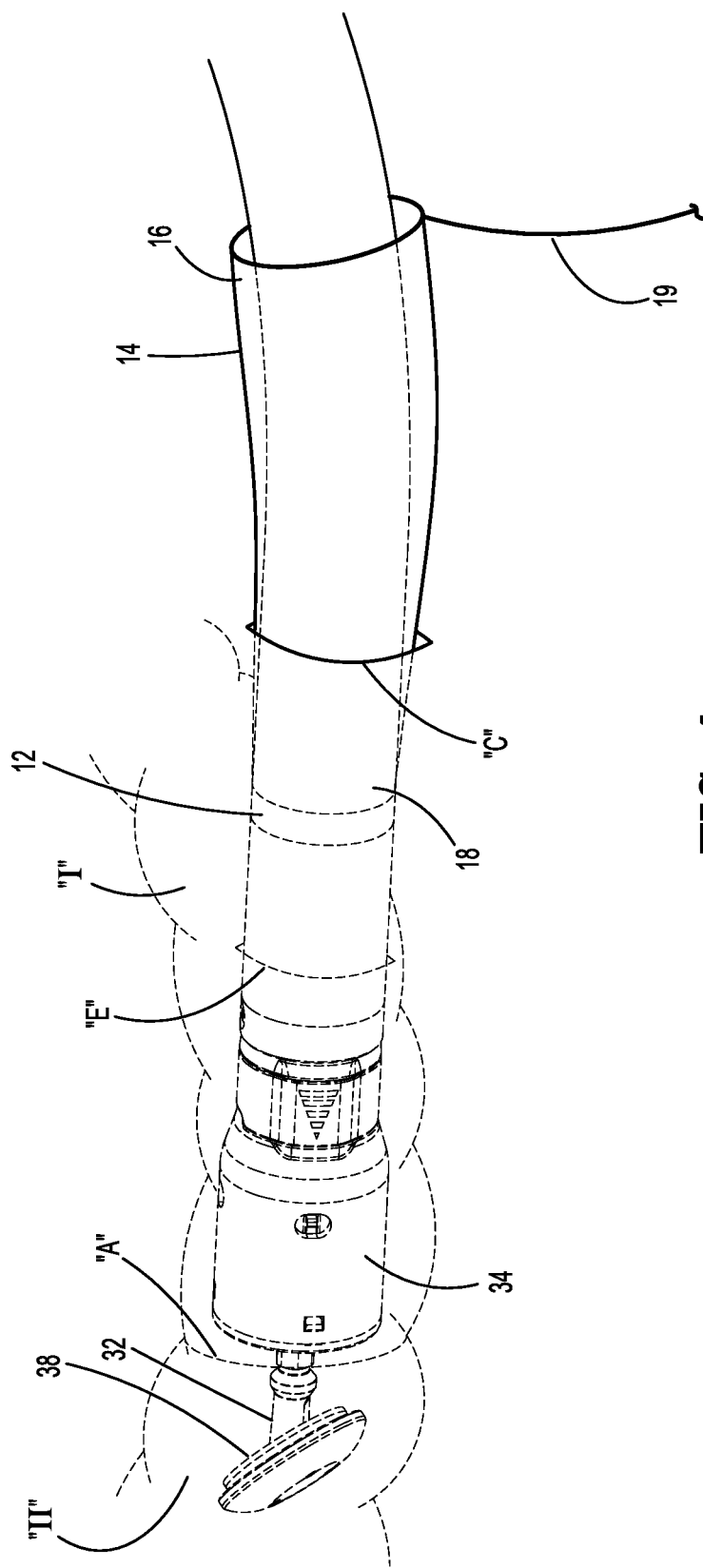
FIG. 4 is an enlarged view of the indicated area of detail shown in FIG. 3.

With reference to FIGS. 3-5, in an exemplary procedure, the circular stapling instrument 20 is introduced into a patient's intestine to join two ends thereof. As depicted in FIG. 3, an abdominal region "AR" of a subject's body generally includes an abdominal wall "AW". For instance, as part of a digestive system of a subject's body, the stomach (not shown) and the intestines "I" are supported in the abdominal cavity "AC." In some cases, it may be necessary to remove a section of the patient's intestine, whether due to cancer, diverticulitis, or other diseases of the GI tract, and re-join the healthy sections of the intestine "I".

As shown in FIGS. 3 and 4, in embodiments an incision "C" is formed in the abdominal wall "AW". An enterostomy, i.e., an opening "E", is formed in a wall of the intestine "I" to permit passage of the circular stapling instrument 20 into the lumen of the intestine "I". As shown in FIG. 4, a portion of the intestine is removed (not shown), and the circular stapling instrument 20 is advanced to form an anastomosis "A", whereby the two portions of the intestine "I" and "II" adjacent the removed portion are joined by the circular stapling instrument 20. The general operation of the circular stapling instrument 20 is described above. Briefly, the anvil 38 of the circular stapling instrument 20 is advanced from a first segment of the intestine "I" having the enterostomy "E", through a first intestinal end segment, and then through a second intestinal end segment into a second segment of the intestine "II". The circular stapling instrument 20 is fired to join the first intestinal end segment of the intestine "I" to the second intestinal end segment of the second segment of the intestine "II".

At this point, as noted above, due to its presence within the intestine "I" and second portion of the intestine "II", the distal portion of the circular stapling instrument 20, including the anvil 38 and the cartridge assembly 34 are contaminated due to their exposure to any fecal matter and flora within the intestine "I" and the second portion of the intestine "II". Thus, as depicted in FIGS. 4 and 5, after the circular stapling instrument 20 has been fired and the anastomosis "A" has been formed, the clinician may use a grasper "G" or similar device to grab the proximal portion 16 of the tubular body 14 of the wound protector 10 and pull the proximal portion 16 of the tubular body 14 so that it everts over the end effector 26 of the circular stapling instrument 20, encompassing both the anvil 38 and the cartridge assembly 24 therein. As depicted in FIG. 5, in embodiments the anvil 38 may pivot, to assist in its removal from the intestine "I" and the patient's body.

As shown in FIG. 5, in embodiments, proximally pulling the circular stapling instrument 20 (indicated by arrow "B" in FIG. 5) assists in both everting the tubular body 14 over the end effector 26 of the circular stapling instrument 20 and encompassing both the anvil 38 and the cartridge assembly 34 therein.

Figure 6:
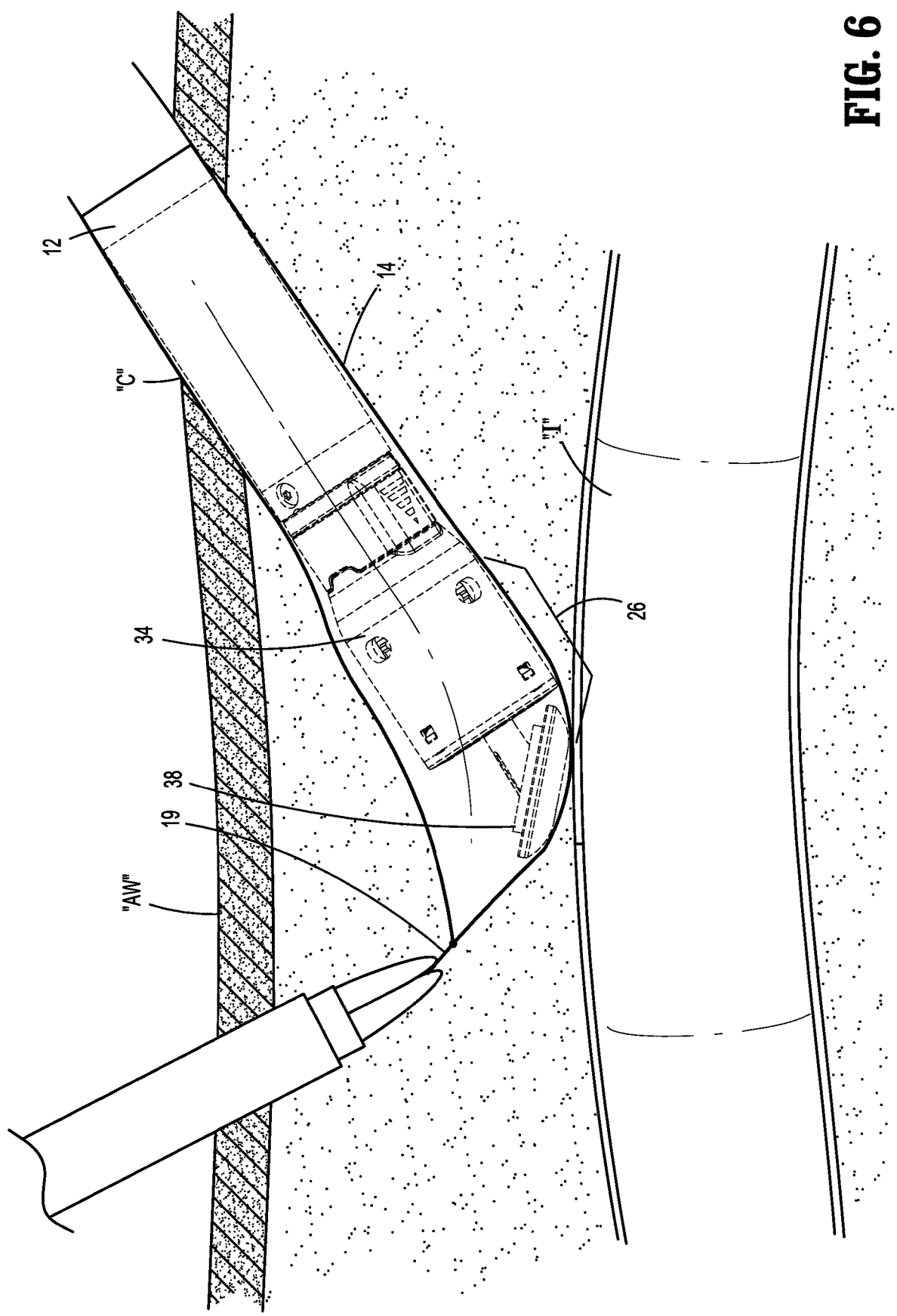
FIG. 6 is a side view showing the closing of the wound protector shown in FIG. 5.
Figure 7:
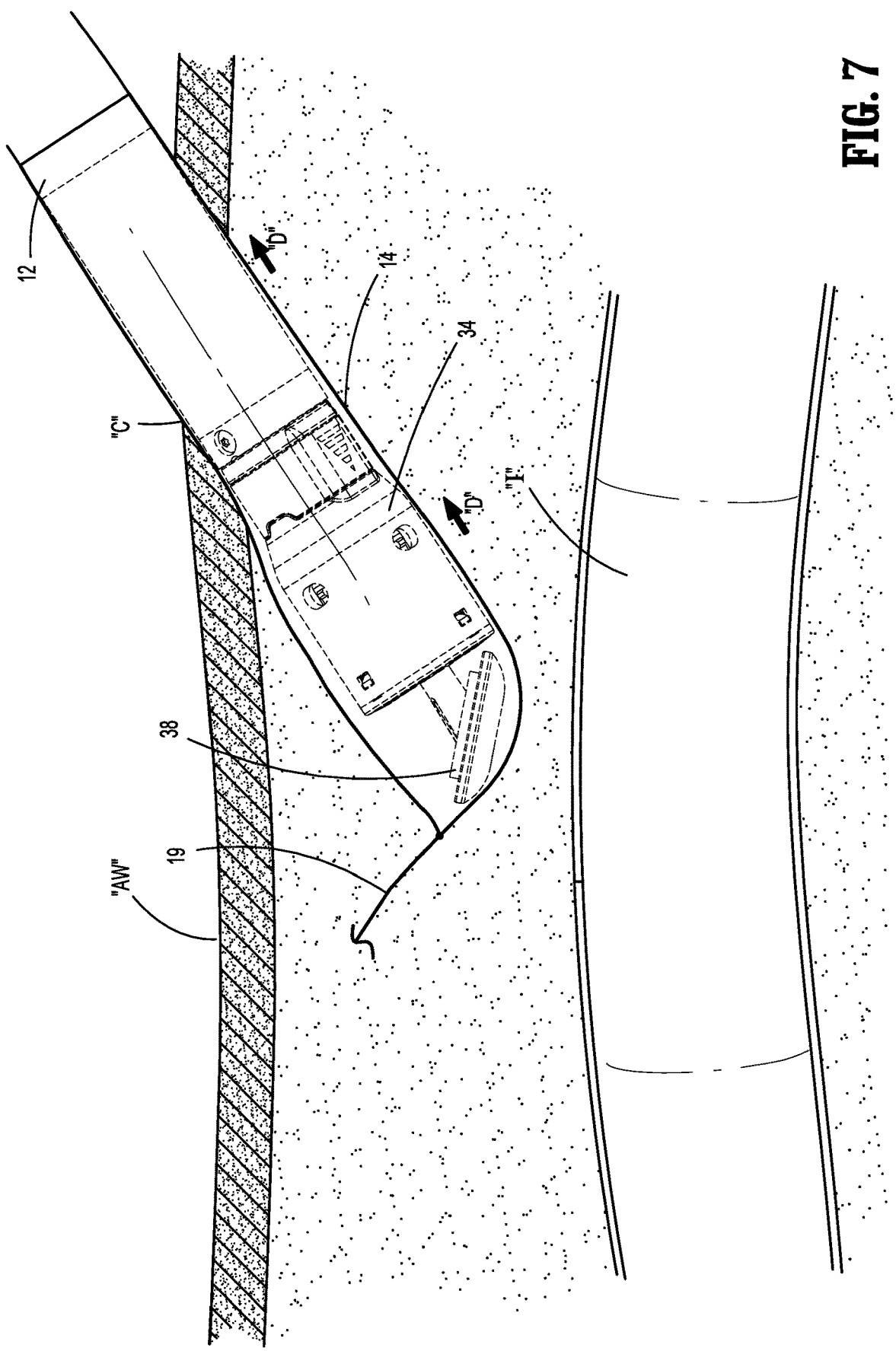
FIG. 7 is a side view showing the removal of the closed wound protector and the surgical circular stapling instrument shown in FIG. 6 from a patient's body.

Once the proximal portion 16 of the tubular body 14 of the wound protector 10 everts over the end effector 26 of the circular stapling instrument 20, as depicted in FIG. 6, the grasper "G" may be used to pull the pull string 19, thereby closing the opening at the proximal portion of the wound protector 10 and containing the end effector 26 of the circular stapling instrument 20 therein. In some embodiments, everting the proximal portion 16 of the tubular body 14 over the end effector 26 of the circular stapling instrument 20 may also encompass tissue specimen(s) therein (not shown).

At this point, proximally pulling the circular stapling instrument 20 (indicated by arrows "D" in FIG. 7) removes the circular staling instrument 20 from the patient's body through the incision "C" of the abdominal wall "AW".

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical stapling instrument, comprising:
   a handle;
   an end effector including a stapling apparatus;
   an adapter connecting the handle and the end effector;
   a wound protector having a tubular body possessing a first portion and a second portion, the tubular body defining a longitudinal bore that extends between the first portion and the second portion of the tubular body, the adapter passing through the longitudinal bore of the tubular body, the first portion of the wound protector configured to be everted from a first position at a proximal location adjacent the adapter to a second position at a distal location so that the wound protector covers the end effector of the surgical stapling instrument; and
   a fixation ring attaching the second portion of the tubular body to the adapter.

2. The surgical stapling instrument of claim 1, wherein the first portion of the tubular body defines an opening, and the surgical stapling instrument further includes a pull string at the first portion of the tubular body about the opening.

3. The surgical stapling instrument of claim 2, wherein the pull string is in a cuff at the first portion of the tubular body about the opening.

4. The surgical stapling instrument of claim 1, wherein the tubular body of the wound protector is formed of a biocompatible material.

5. The surgical stapling instrument of claim 4, wherein the tubular body of the wound protector is formed of nylon, urethane, ripstop nylon, or latex.

* * * * *